(12) United States Patent
Hershey (10) Patent No.: US 9,381,360 B2
(45) Date of Patent: Jul. 5, 2016

(54) SYSTEM AND METHOD FOR DELIVERING MODULATED SUB-THRESHOLD THERAPY TO A PATIENT

(71) Applicant: Boston Scientific Neuromodulation Corporation, Valencia, CA (US)

(72) Inventor: Bradley L. Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/600,649

(22) Filed: Jan. 20, 2015

(65) Prior Publication Data

US 2015/0217117 A1 Aug. 6, 2015

Related U.S. Application Data

(60) Provisional application No. 61/936,269, filed on Feb. 5, 2014.

(51) Int. Cl.
*A61N 1/00* (2006.01)
*A61N 1/36* (2006.01)
*A61N 1/372* (2006.01)

(52) U.S. Cl.
CPC ........ *A61N 1/36175* (2013.01); *A61N 1/36125* (2013.01); *A61N 1/36164* (2013.01); *A61N 1/36178* (2013.01); *A61N 1/37247* (2013.01)

(58) Field of Classification Search
CPC ........... A61N 1/36139; A61N 1/36164; A61N 1/36125; A61N 1/36167; A61N 1/36171; A61N 1/36175; A61N 1/36178; A61N 1/36189; A61N 1/36192; A61N 1/36196
See application file for complete search history.

(56) References Cited

U.S. PATENT DOCUMENTS

| 5,938,690 A | 8/1999 | Law et al. |
| 5,941,906 A | 8/1999 | Barreras, Sr. et al. |
| 6,516,227 B1 | 2/2003 | Meadows et al. |

(Continued)

FOREIGN PATENT DOCUMENTS

| WO | WO-2006029257 A2 | 3/2006 |
| WO | WO-2006135791 A2 | 12/2006 |
| WO | WO-2015119768 A1 | 8/2015 |

OTHER PUBLICATIONS

Doan, Que T., "System and method for delivering modulated sub-threshold therapy to a patient", U.S. Appl. No. 61/832,088, filed Jun. 6, 2013.

(Continued)

*Primary Examiner* — Robert N Wieland
(74) *Attorney, Agent, or Firm* — Schwegman Lundberg & Woessner, P.A.

(57) ABSTRACT

A neuromodulation system configured for providing sub-threshold neuromodulation therapy to a patient. The neuromodulation system comprises a plurality of electrical terminals configured for being respectively coupled to a plurality of electrodes, modulation output circuitry configured for delivering electrical energy to the electrical terminals in accordance with at least one modulation parameter, thereby providing therapy to the patient at a sub-threshold level and control circuitry configured for controlling the modulation output circuitry in a manner that pseudo-randomly varies a value of the at least one modulation parameter based on a previous value of the at least one modulation parameter, such that the delivered electrical energy is continually maintained at the sub-threshold level.

20 Claims, 8 Drawing Sheets

(56) References Cited

U.S. PATENT DOCUMENTS

| | | | |
|---|---|---|---|
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,627,384 B2 | 12/2009 | Ayal et al. | |
| 7,650,184 B2 | 1/2010 | Walter | |
| 7,979,133 B2 | 7/2011 | Feler et al. | |
| 7,987,000 B2 | 7/2011 | Moffitt et al. | |
| 8,019,439 B2 | 9/2011 | Kuzma et al. | |
| 8,160,328 B2 | 4/2012 | Goetz et al. | |
| 8,180,129 B2 | 5/2012 | Goetz et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,380,318 B2 | 2/2013 | Kishawi et al. | |
| 8,412,345 B2 | 4/2013 | Moffitt | |
| 8,437,857 B2 | 5/2013 | Moffitt et al. | |
| 8,455,716 B2 | 6/2013 | Huang et al. | |
| 8,504,147 B2 | 8/2013 | Deem et al. | |
| 8,594,785 B2 | 11/2013 | Bradely | |
| 8,615,300 B2 | 12/2013 | Feler et al. | |
| 8,649,874 B2 | 2/2014 | Alataris et al. | |
| 8,660,653 B2 | 2/2014 | Kothandaraman et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,700,178 B2 | 4/2014 | Anderson | |
| 8,731,675 B2 | 5/2014 | Ranu et al. | |
| 8,751,009 B2 | 6/2014 | Wacnik | |
| 2003/0139781 A1 | 7/2003 | Bradley et al. | |
| 2004/0116978 A1 | 6/2004 | Bradley | |
| 2005/0060008 A1* | 3/2005 | Goetz | A61N 1/36071 607/48 |
| 2006/0015153 A1 | 1/2006 | Gliner et al. | |
| 2007/0150036 A1 | 6/2007 | Anderson | |
| 2007/0167991 A1* | 7/2007 | DiLorenzo | A61N 1/36082 607/45 |
| 2008/0077192 A1 | 3/2008 | Harry et al. | |
| 2008/0188909 A1 | 8/2008 | Bradley | |
| 2009/0118777 A1 | 5/2009 | Iki et al. | |
| 2009/0196472 A1 | 8/2009 | Goetz et al. | |
| 2009/0198306 A1 | 8/2009 | Goetz et al. | |
| 2009/0204173 A1 | 8/2009 | Fang et al. | |
| 2010/0010566 A1 | 1/2010 | Thacker et al. | |
| 2010/0023090 A1 | 1/2010 | Jaax et al. | |
| 2010/0121409 A1 | 5/2010 | Kothandaraman et al. | |
| 2010/0249875 A1 | 9/2010 | Kishawi et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0213440 A1* | 9/2011 | Fowler | A61N 2/006 607/45 |
| 2011/0213442 A1* | 9/2011 | Pless | A61N 1/36178 607/45 |
| 2011/0282414 A1 | 11/2011 | Kothandaraman et al. | |
| 2011/0295332 A1* | 12/2011 | Osorio | A61B 5/0476 607/3 |
| 2012/0059446 A1 | 3/2012 | Wallace et al. | |
| 2012/0083709 A1 | 4/2012 | Parker et al. | |
| 2012/0101547 A1* | 4/2012 | Jensen | A61N 1/36067 607/45 |
| 2012/0197336 A1* | 8/2012 | Su | A61N 1/36007 607/41 |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0296395 A1* | 11/2012 | Hamann | A61N 1/36135 607/59 |
| 2013/0018437 A1* | 1/2013 | De Ridder | A61N 1/36171 607/51 |
| 2013/0066411 A1 | 3/2013 | Thacker et al. | |
| 2013/0116752 A1 | 5/2013 | Parker et al. | |
| 2013/0268021 A1 | 10/2013 | Moffitt | |
| 2013/0296975 A1 | 11/2013 | Lee et al. | |
| 2014/0046407 A1* | 2/2014 | Ben-Ezra | A61N 1/0556 607/62 |
| 2014/0081349 A1 | 3/2014 | Lee et al. | |
| 2014/0213926 A1* | 7/2014 | Vaidyanathan | A61N 1/36067 600/545 |
| 2014/0222113 A1* | 8/2014 | Gliner | A61N 1/3606 607/62 |
| 2014/0277267 A1 | 9/2014 | Vansickle et al. | |

OTHER PUBLICATIONS

Kothandaraman, Sridhar, et al., "System and Method for Connecting Devices to a Neurostimulator", U.S. Appl. No. 61/694,695, filed Aug. 29, 2012.

Lee, Dongchul, "Neurostimulation System for Defining a Generalized Ideal Multipole Configuration", U.S. Appl. No. 61/452,965, filed Mar. 15, 2011.

Rao, Prakash, et al., "Technique for Linking Electrodes Together During Programming of Neurostimulation System", U.S. Appl. No. 61/561,760, filed Nov. 18, 2011.

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

Warman, Eduardo N., et al., "Modeling the Effects of Electric Fields on Nerve Fibers: Determination of Excitation Thresholds", IEEE Transactions on Biomedical Engineering, vol. 39, No. 12, Dec. 1992.

Zhu, Changfang, et al., "Neurostimulation System for Estimating Desired Stimulation Amplitude for Electrode Configuration", U.S. Appl. No. 61/427,027, filed Dec. 23, 2010.

Zhu, Changfang, et al., "Neurostimulation System for Implementing Model-Based Estimate of Neurostimulation Effects", U.S. Appl. No. 61/427,059, filed Dec. 23, 2010.

"International Application Serial No. PCT/US2015/012030, International Search Report mailed Apr. 21, 2015", 5 pgs.

"International Application Serial No. PCT/US2015/012030, Written Opinion mailed Apr. 21, 2015", 7 pgs.

* cited by examiner

SYSTEM AND METHOD FOR DELIVERING MODULATED SUB-THRESHOLD THERAPY TO A PATIENT

CLAIM OF PRIORITY

This application claims the benefit of priority under 35 U.S.C. §119(e) of U.S. Provisional Parent Application Ser. No. 61/936,269, filed on Feb. 5, 2014, which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying stimulation leads, which are implanted at the desired stimulation site, and an implantable neuromodulation device (e.g., an implantable pulse generator (IPG)) implanted remotely from the stimulation site, but coupled either directly to the neuromodulation leads) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected stimulation parameters.

Electrical modulation energy may be delivered from the neuromodulation device to the electrodes in the form of an electrical pulsed waveform. Thus, electrical energy may be controllably delivered to the electrodes to therapeutically modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses (which may be considered electrical pulse parameters) provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the handheld external control device to modify the electrical modulation energy provided by the neuromodulation device system to the patient. Thus, in accordance with the modulation parameters programmed by the external control device, electrical pulses can be delivered from the neuromodulation device to the electrode(s) to modulate a volume of tissue in accordance with a set of modulation parameters and provide the desired efficacious therapy to the patient. The best modulation set will typically be one that delivers modulation energy to the volume of tissue that must be modulated in order to provide the therapeutic benefit (e.g., treatment of pain), while minimizing the volume of non-target tissue that is modulated.

However, the number of electrodes available combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation systems may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum stimulation parameters to be determined based on patient feedback or other means and to subsequently program the neuromodulation device with the optimum modulation parameter sets.

For example, in order to achieve an effective result from conventional SCS, the lead or leads must be placed in a location, such that the electrical modulation energy (in this case, electrical stimulation energy) creates a sensation known as paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SOS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint volume of activation (VOA) or areas correlating to the pain, Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high frequency pulsed electrical energy and/or low pulse width electrical energy) can be effective in providing neuromodulation therapy for chronic pain without causing paresthesia.

In both conventional neuromodulation therapy described above where the patient feels paresthesia (super-threshold neuromodulation therapy) and sub-threshold neuromodulation therapy, common complications, caused due to cellular and synaptic mechanisms, include neurological phenomena, such as accommodation, adaption, and habituation, all of which entail a diminished neural response over time when there exists continuous input (in this case, electrical stimulation). For the purposes of this specification, we will use the term "accommodation" to generally refer to any mechanism that diminishes neural response due to continuous input.

Oftentimes, due to accommodation, a clinician may identify a modulation parameter set where a patient is obtaining great paresthesia, but when the clinician subsequently returns to this modulation parameter set, even within the same programming session, the patient may no longer receive the same paresthesia. While this complication may be addressed a little more easily in the case of super-threshold neuromodulation therapy, it is more difficult in the case of sub-threshold neuromodulation therapy because the patient may not be able to determine, due to the lack of paresthesia, whether, and when, accommodation has occurred. Thus, without realizing that accommodation has occurred, the neuromodulation energy may continue to be delivered to the patient without providing little or no benefit to the patient. Furthermore, previous methods of preventing accommodation involve varying the modulation parameters frequently such that the neuronal fibers do not acclimate to any particular set of modulation parameters. This method, while somewhat efficacious, is nevertheless limited in its efficacy given that the patterns of variance of the modulation parameters typically do not resemble physiologically relevant signals, due to which the neuronal fibers eventually accommodate to this type of neuromodulation therapy.

There, thus, remains a need for an improved method and system that avoids or otherwise manages neurological accommodation caused by sub-threshold neuromodulation.

SUMMARY OF THE INVENTION

In accordance with a first aspect of the present inventions, a method of providing neuromodulation therapy is provided. The method comprises delivering electrical energy to tissue of the patient in accordance with at least one modulation parameter, thereby providing therapy to the patient at a sub-threshold level (e.g., pulse rate greater than 1500 Hz, pulse width less than 100 μs), and pseudo-randomly varying a value of the at least one modulation parameter based on a previous value of the at least one modulation parameter, such that the delivered electrical energy is continually maintained at the sub-threshold level.

The method further comprises calculating the pseudo-randomly varied value based on a function of the previous value and a pseudo-randomly generated number, and delivering electrical energy having the pseudo-randomly varied value of the at least one modulation parameter. The pseudo-randomly varied value may be varied by both increasing and decreasing the value around a mean value of the at least one modulation parameter. The modulation parameter may be a pulse amplitude, a pulse duration or a pulse rate. The modulation parameter may be pseudo-randomly varied within a limited range. The limited range may be defined by user-input.

The pseudo-random variance of the at least one modulation parameter mimics a physiologically relevant signal. The method further comprises delivering electrical energy in accordance with a plurality of pseudo-randomly varied values of the at least one modulation parameter, such that neural tissue is stimulated without undergoing neurological accommodation.

In accordance with a second aspect of the present inventions, a neuromodulation system comprises a plurality of electrical terminals configured for being respectively coupled to a plurality of electrodes, modulation output circuitry configured for delivering electrical energy to the electrical terminals in accordance with at least one modulation parameter, thereby providing therapy to the patient at a sub-threshold level (e.g., pulse rate greater than 1500 Hz, pulse width less than 100 μs), and control circuitry configured for controlling the modulation output circuitry in a manner that pseudo-randomly varies a value of the at least one modulation parameter based on a previous value of the at least one modulation parameter, such that the delivered electrical energy is continually maintained at the sub-threshold level.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
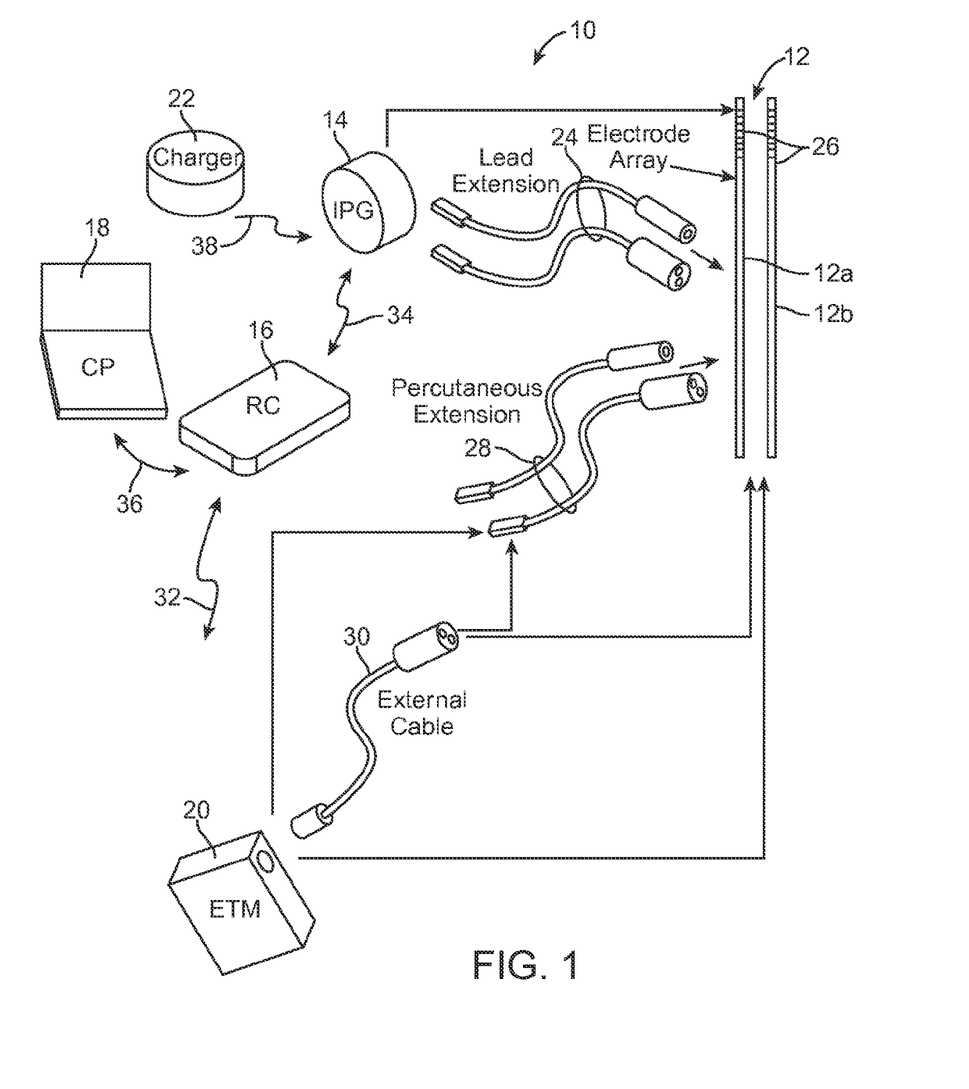
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a standalone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
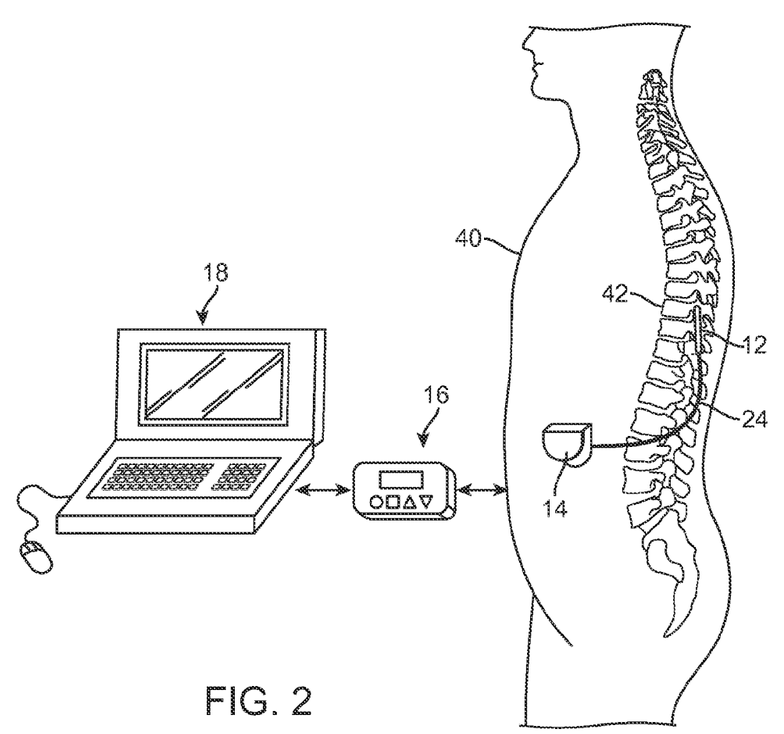
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

The IPG 14 comprises an outer case 40 for housing the electronic and other components (described in further detail below), and a connector 42 to which the proximal ends of the neuromodulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a pulse generation circuitry that provides electrical modulation energy to the electrodes 26 in accordance with a set of modulation parameters. Such parameters may include electrode combinations, which define the electrodes that are activated as anodes (positive), cathodes (negative), and turned off (zero). The modulation parameters may further include pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG outer case 40. Electrical energy may be transmitted to the tissue in a monopolar or multipolar (for example, bipolar, tripolar and similar configurations) fashion or by any other means available.

The IPG 14 may be operated in either a super-threshold delivery mode or a sub-threshold delivery mode. While in the super-threshold delivery mode, the IPG 14 is configured for delivering electrical modulation energy that provides super-threshold therapy to the patient (in this case, causes the patient to perceive paresthesia). For example, an exemplary super-threshold pulse train may be delivered at a relatively high pulse amplitude (e.g., 5 ma), a relatively low pulse rate (e.g., less than 1500 Hz, preferably less than 500 Hz), and a relatively high pulse width (e.g., greater than 100 µs, preferably greater than 200 µs).

While in the sub-threshold delivery mode, the IPG 14 is configured for delivering electrical modulation energy that provides sub-threshold therapy to the patient (in this case, does not cause the patient to perceive paresthesia). For example, an exemplary sub-threshold pulse train may be delivered at a relatively low pulse amplitude (e.g., 2.5 ma), a relatively high pulse rate (e.g., greater than 1500 Hz, preferably greater than 2500 Hz), and a relatively low pulse width (e.g., less than 100 µs, preferably less than 50 µs).

Figure 3:
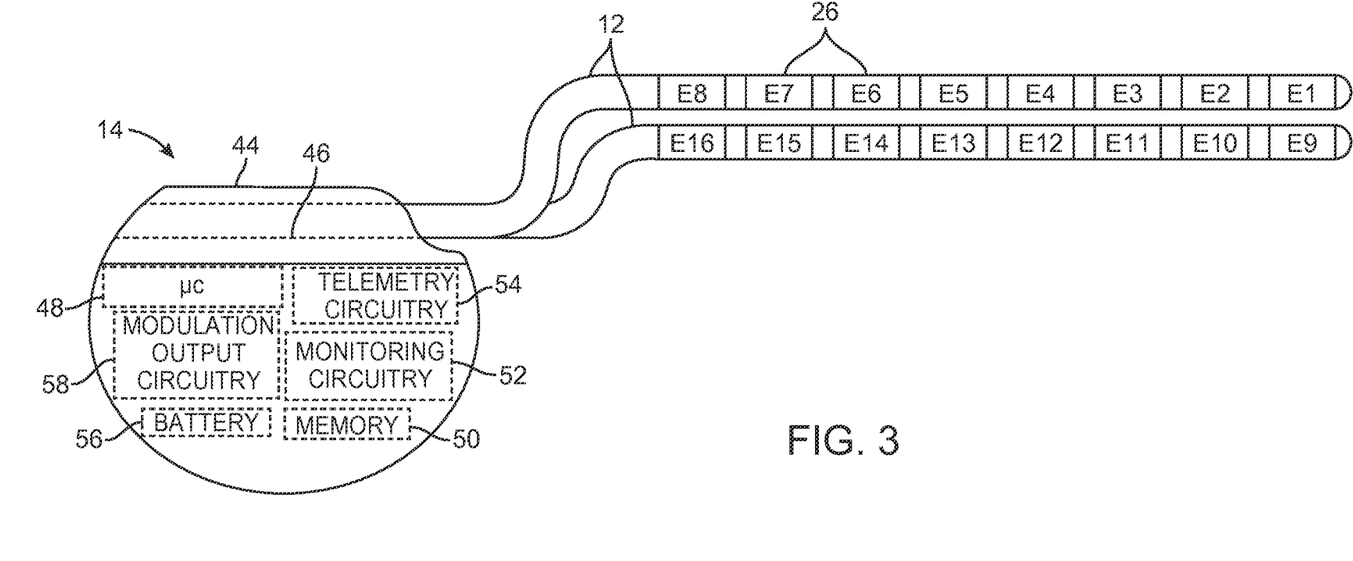
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 48, memory 50, a battery 52, telemetry circuitry 54, monitoring circuitry 56, modulation output circuitry 58, and other suitable components known to those skilled in the art. The microcontroller 48 executes a suitable program stored in memory 50, for directing and controlling the neuromodulation performed by IPG 14. Significant to the present inventions, the memory 50 may additionally store a Bayesian algorithm based on which the microcontroller 48 pseudo-randomly varies the modulation parameters of a particular program to avoid neurological accommodation, as will be discussed in further detail below.

Telemetry circuitry 54, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 54 is also configured for transmitting status data to the RC 16 and/or CP 18 in an appropriate modulated carrier signal. The battery 52, which may be a rechargeable lithium-ion or lithium-ion polymer battery, provides operating power to IPG 14. The monitoring circuitry 56 is configured for monitoring the present capacity level of the battery 43.

The modulation output circuitry 58 is controlled by the microcontroller 48 to provide electrical modulation energy in the form of a pulsed electrical waveform to the electrodes 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12b is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode.

Any of the electrodes E1-E16 and case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (sourcing current), negative (sinking current), or off (no current) polarity in any of the k timing channels.

Figure 4:
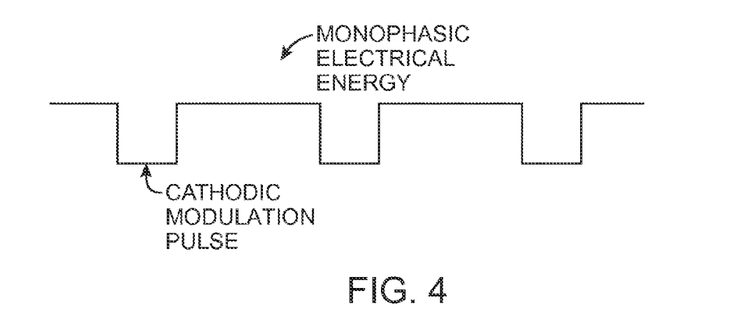
FIG. 4 is a plot of monophasic cathodic electrical modulation energy.
Figure 5A:
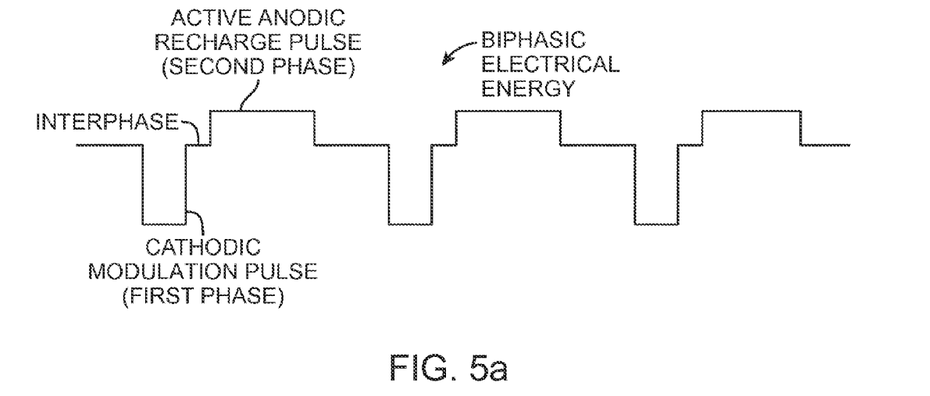
FIG. 5a is a plot of biphasic electrical modulation energy having a cathodic modulation pulse and an active charge recovery pulse.
Figure 5B:
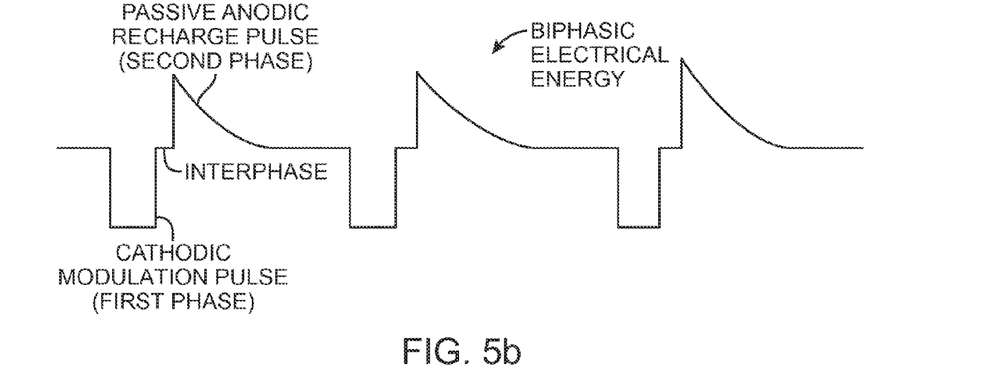
FIG. 5b is a plot of biphasic electrical modulation energy having a cathodic modulation pulse and a passive charge recovery pulse.

The modulation energy may be delivered between electrodes as monophasic electrical energy or multiphasic electrical energy, Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) neuromodulation pulse and an anodic (positive) recharge pulse that is generated after the neuromodulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse).

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the modulation in accordance with the control signals.

More significant to the present inventions, the SCM system 10, in an effort to avoid a state of neurological accommodation, is configured for pseudo-randomly varying the modulation parameters based on which electrical energy is delivered in a manner that more closely resembles physiologically relevant electrical signals as recognized by neural mechanisms in the dorsal horn. Neurological accommodation is a common complication in the area of neuromodulation therapy, which has been previously combatted by introducing variance in the modulation parameters to prevent the neural tissue from acclimating to any particular set of modulation parameters. As mentioned previously, while this technique has been somewhat successful in delaying accommodation, it has been observed that the neural tissue eventually acclimates to the introduced pattern of variance such that the neural tissue ultimately succumbs to neurological accommodation.

In particular, the SCM system 10 is configured for introducing "noise" into a particular neuromodulation therapy regimen to help avoid neurological accommodation because the noise has been observed to be a more physiologically-relevant signal that is adept at reducing pain, specifically in relation to the Gate Control Theory popularized by Ronald Melzack and Patrick Wall.

Figure 6A:
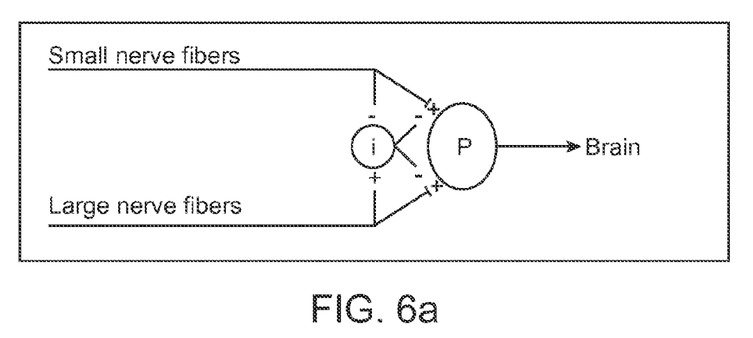
FIG. 6a is a block diagram illustrating the Gate Control Theory when neither small nerve fibers nor large nerve fibers are stimulated.
Figure 6B:
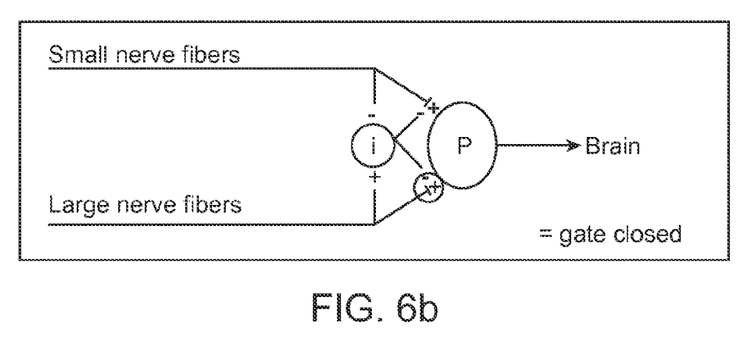
FIG. 6b is the block diagram of FIG. 6a, illustrating the Gate Control Theory when more large nerve fibers are stimulated.
Figure 6C:
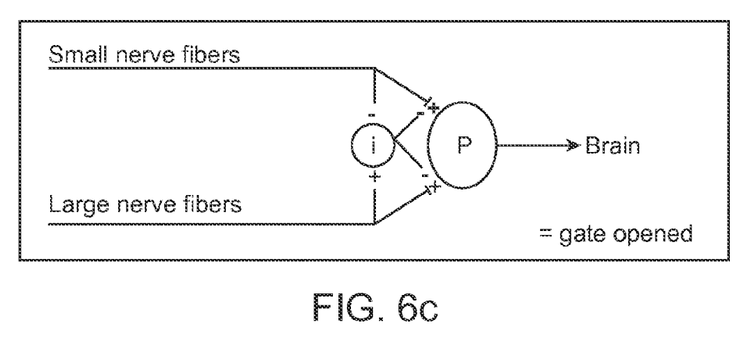
FIG. 6c is the block diagram of FIG. 6a, illustrating the Gate Control Theory when more small nerve fibers are stimulated.

Referring to FIGS. 6a, 6b and 6c, as per the Gate Control Theory, a gating mechanism exists within the dorsal horn of the spinal cord wherein small nerve fibers (pain receptors) and large nerve fibers (normal receptors) synapse both on projection neurons ("P") which go up to the brain and on inhibitory interneurons ("I") within the dorsal horn. When there is no input at all, the inhibitory interneuron I prevents the projection neuron P from sending signals to the brain (i.e., the gate is closed) (FIG. 6a). Normal somatosensory input occurs when the large fiber neurons (or mostly large fiber neurons) are stimulated, leading to both the inhibitory neuron I and the project neuron P being stimulated, but the inhibitory neuron I prevents the projection neuron P from sending signals to the brain (i.e., the gate is dosed) (FIG. 6b). When there is more small-fiber stimulation, however, the inhibitory neuron I is inactivated and the projection neuron P sends signals of pain to the brain (I.e., the gate is open) (FIG. 6c).

Thus, as per the Gate Control Theory, stimulation of the large nerve fibers activates the inhibitory neuron I that prevents the projection neuron P from sending pain signals to the brain, However, it should be appreciated that if stimulation is prolonged, the large fibers tend to adapt, producing an increase in small-fiber activity and as a result, the gate is opened, instead of remaining dosed. Thus, the goal for pain management is to increase large fiber activity sporadically such that the gate remains dosed but to ensure that large fiber activity is not prolonged too long such that the large nerves adapt to the stimulation.

Applying these concepts in the context of neuromodulation, starting with conventional neuromodulation therapy, when electrical pulses are delivered to the dorsal columns at a tonic rate, the large nerve fibers are entrained to all fire at the same rate, This has the effect of both projecting to the brain (to account for paresthesia) and also synapsing on the inhibitory interneuron I, thus dosing the gate, which prevents or reduces the perception of pain as per the Gate Control Theory discussed above. However, due to the constant stimulus, the large never fibers tend to adapt, thereby increasing the activity of small nerve fibers and eventually opening the gate, thus limiting the efficacy of the treatment.

In the case of sub-threshold neuromodulation therapy, it is postulated that at sub-threshold amplitudes, many large nerve fibers are on the brink of firing, but, due to the moment-by-moment micromotion of the spinal cord in relation to the implanted neuromodulation lead 12, the likelihood of firing of the large nerve fibers is more stochastic than tonic. In other words, in contrast to conventional neuromodulation therapy, the large nerve fibers do not fire constantly at every pulse, but rather build up to occasionally fire, the probability of each firing depending on how the nerve fibers reacted at a previously delivered electrical pulse of the sub-threshold neuromodulation regimen. Multiplying this phenomenon in a larger population of nerves with varying sizes and distances, the net effect is the introduction of noise into the system. This noise may be a more physiologically relevant signal because it represents a more natural balance of activity between the small nerve fibers and the large nerve fibers.

Notwithstanding the natural introduction of this noise into the system in sub-threshold neuromodulation therapy, the SCM system 10 is configured for taking this concept even further, and artificially introducing noise in the temporal and spatial firing patterns of the dorsal column fibers (i.e., large nerve fibers) to best resemble physiologically relevant signals. To this end, rather than introducing random noise, the SCM system 10 is configured for introducing noise in a Bayesian pattern, which is thought to be more physiologically relevant than random noise. The term "Bayesian" refers to statistical methods that assign probabilities to current or future events based on previous experience and/or previously collected data.

In particular, the value of a modulation parameter of a particular sub-threshold modulation program may be pseudo-randomly varied based on a previous value (or values) of the modulation parameter, while maintaining sub-threshold levels. This pseudo-random pattern of variance is postdated to generate electrical signals in the dorsal horn that better mimic the stochastic firing pattern of the neuronal fibers rather than that generated by a conventional predetermined pattern of variance or a random pattern of variance of the modulation patterns. Thus, by closely mimicking naturally occurring and physiologically relevant signal patterns of the dorsal horn, the SCM system 10 is configured for avoiding neurological accommodation caused by prolonged electrical stimulation.

In determining the pseudo-randomly varied values of the modulation parameter(s), the SCM system 10 is configured for consulting a Bayesian algorithm stored in the memory. When creating this algorithm, past successful patterns of variance in modulation parameters and/or experiments that led large nerve fibers to fire stochastically without succumbing to adaptation may be taken into account.

It should be appreciated that the introduction of noise is not meant to interfere with the prescribed neuromodulation program, but rather simply makes changes, within a range, to the neuromodulation program to prolong its efficacy by helping avoid neurological accommodation. Thus, the basic shape of the electrical pulse train will be maintained while introducing a layer of noise created by the pseudo-random variance of one or more modulation parameters.

Although this technique may be used for other modulation parameters (e.g., burst rate, etc.), pseudo-randomly varying the pulse amplitude, pulse width and pulse frequency is anticipated to be most effective for avoiding neurological accommodation. Thus, the following discussion will focus exclusively on pseudo-randomly varying pulse amplitude, pulse width and pulse frequency for illustrative purposes.

Figure 7A:
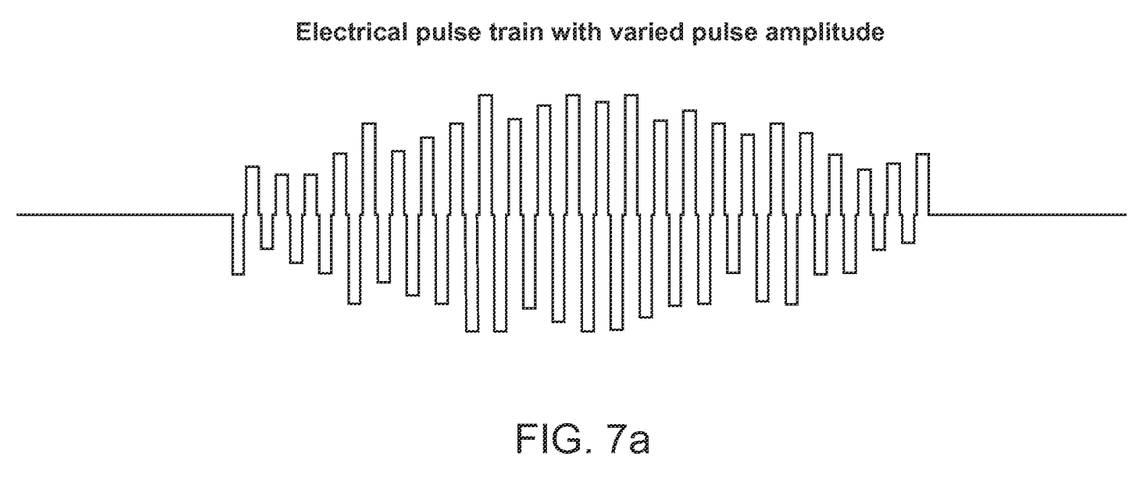
FIG. 7a is a timing diagram illustrating an electrical pulse train delivered by the SCM system of FIG. 1, wherein the pulse amplitude is pseudo-randomly varied.

For example, as shown in FIG. 7a, the SCM system 10 automatically varies the pulse amplitude over time based on the stored Bayesian algorithm. As shown in FIG. 7a, the pulse amplitude is constantly varied within a range. In the exemplary electrical pulse train of FIG. 7a, the pulse amplitude changes seamlessly over time while the remaining modulation parameters remain constant. It should be appreciated that this technique creates dynamically changing pulse amplitudes such that no two pulse amplitudes are identical, although the pulse amplitude stays within the sub-threshold range.

Figure 7B:
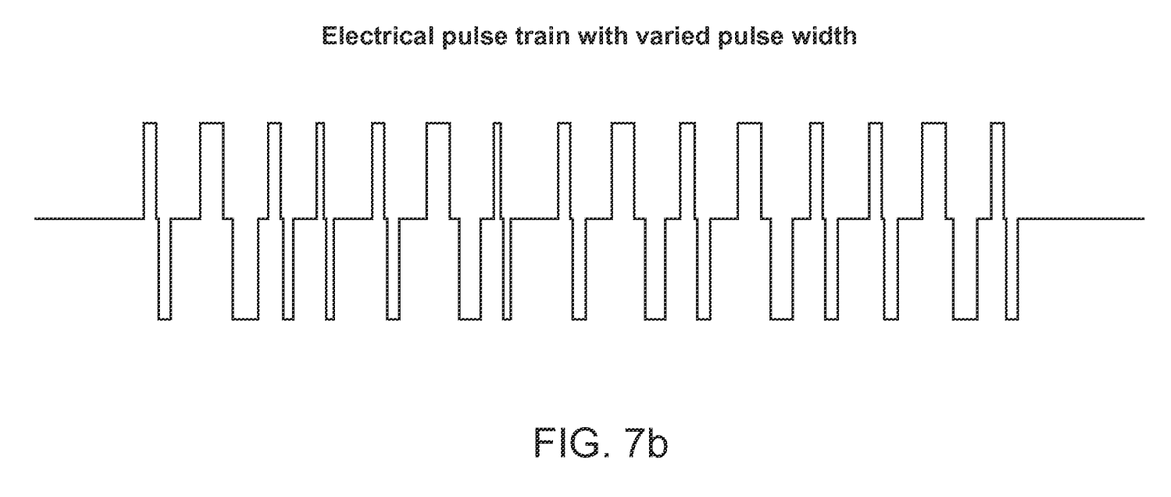
FIG. 7b is a timing diagram illustrating an electrical pulse train delivered by the SCM system of FIG. 1, wherein the pulse width is pseudo-randomly varied.

Similarly, as shown in FIG. 7b, the SCM system 10 automatically varies the pulse width over time based on the stored Bayesian algorithm. Rather than follow a fixed pattern, the pulse width is varied, within a range, such that each value of the pulse width is dependent on a previous value of the pulse width. Similar to the above, in the exemplary electrical pulse train of FIG. 7b, the pulse width changes seamlessly over time (within the sub-threshold range) while the remaining modulation parameters remain constant. Again, as above, no two pulse widths are identical.

Figure 7C:
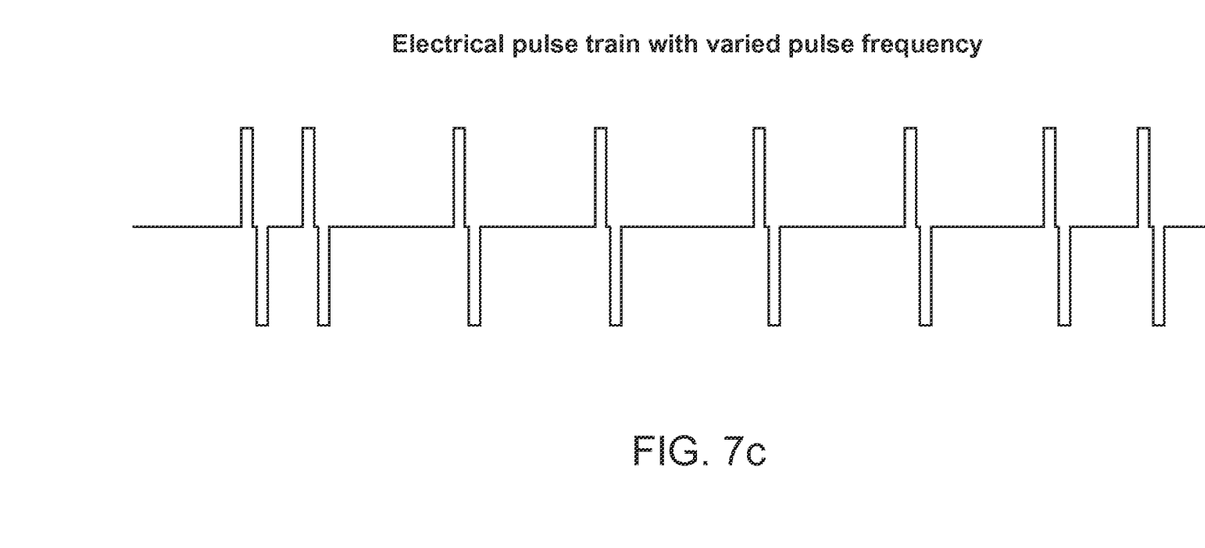
FIG. 7c is a timing diagram illustrating an electrical pulse train delivered by the SCM system of FIG. 1, wherein the pulse frequency is pseudo-randomly varied.

In another example, as shown in FIG. 7c, the SCM system 10 automatically varies the pulse frequency over time based on the stored Bayesian algorithm. The pulse frequency is varied within a range such that each value of the pulse frequency is dependent on a previous value of the pulse frequency. In the exemplary pulse train of FIG. 7c, the pulse frequency changes seamlessly over time such that no two values of the pulse frequency are identical, although all values remain in the sub-threshold range.

To calculate the value of the modulation parameter at any particular pulse, the SCM system 10 is configured to store both a mean value for the modulation parameter and a variable value of the modulation parameter. The mean value of the modulation parameter is the preferred average value of the modulation parameter around which the varied values of the modulation parameter hover, and the variable value represents the range based on which the value of the modulation parameter is pseudo-randomly varied. For example, the mean value for the sub-threshold pulse amplitude may be set at 2 mA, with a variable range of 0.7 mA. Thus, the pulse amplitude may be pseudo-randomly varied between a range of 1.3 mA and 2.7 mA. Similarly, the mean value of the pulse width may be set at 65 μs and the variable value may be set at 10 μs such that the pulse width may be pseudo-randomly varied between a range of 55 μs and 75 μs. Or, the mean value of the pulse frequency may be set at 2000 Hz and the variable value may be set at 500 Hz such that the pulse frequency may be pseudo-randomly varied between a range of 1500 Hz to 2500 Hz. It should be appreciated that the mean value and the variable value may either be automatically determined, or may be manually defined by the user through the CP 18.

In one embodiment, the Bayesian algorithm may automatically generate a pseudo-randomly generated value based on a previous value of the modulation parameter. For example, if the previous value of the pulse amplitude is 2.2 mA, the next value of the pulse amplitude will be based on the previous value of 2.2 mA. In another example, if the previous value of the pulse width is 75 μs, the next value of the pulse width may be based on the previous value of 75 μs. Or, if the previous value of the pulse frequency is 2000 Hz, the next value of he pulse frequency may be based on the previous value of 2000 Hz.

Or, in another embodiment, the Bayesian algorithm may automatically generate a fraction of the variable value based on a fraction of the previous variable value such that the pseudo-randomly varied value of the modulation parameter is the mean value plus or minus the generated fraction of the variable value. For example, if the previous value of the pulse amplitude is 2.2 mA (i.e., mean value 2 mA plus 0.2 mA, which is 30% of the variable value 0.7 mA), the next fraction may be calculated based on the previous fraction of the variable value (30%). In another example, if the previous value of the pulse width is 60 µs (i.e., mean value 65 µs minus 5 µs, which is 50% of the variable value 10 µs), the next fraction may be calculated based on the previous fraction of the variable value (50%). In yet another example, if the previous value of the pulse frequency is 2250 Hz (i.e., mean value 2000 Hz plus 250 Hz, which is 50% of the variable value 500 Hz), the next fraction may be calculated based on the previous fraction of the variable value (50%).

In an optional embodiment, the volume of activation (VOA) of the electrical pulse train may be varied in a variable and pseudo-random fashion around a mean VOA such that the targeted area of therapy receives the same level of sub-threshold neuromodulation therapy. Thus, in this embodiment (not illustrated), both the pulse amplitude and pulse width may be dynamically and pseudo-randomly varied as long as the VOA remains within a sub-threshold range.

Because of the pseudorandom variance of the modulation parameter(s), the large nerve fibers do not fire at a predictable rate, but rather build up to fire occasionally in an unpredictable pattern, thereby introducing noise into the system. As discussed above, this noise is thought to mimic a more natural and physiologically relevant signal in the dynamics of the large nerve fibers and small nerve fibers and the opening and closing of the gate as illustrated in FIGS. 6a, 6b and 6c, and to prevent the large nerve fibers from adapting to any fixed pattern of variance in the neuromodulation therapy, thereby rendering it efficacious for a longer period of time, if not indefinitely.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
   providing a sub-threshold therapy to the patient, including delivering electrical energy to tissue of the patient in accordance with at least one modulation parameter at a sub-threshold level such that the delivered electrical energy is not perceived by the patient but is therapeutically effective for the sub-threshold therapy; and
   pseudo-randomly varying a value of the at least one modulation parameter based on a previous value of the at least one modulation parameter, wherein the at least one modulation parameter is pseudo-randomly varied within a limited range to continually maintain the delivered electrical energy at the sub-threshold level in which the delivered electrical energy is therapeutically effective for the sub-threshold therapy and is not perceived by the patient.

2. The method of claim 1, further comprising calculating the pseudo-randomly varied value of the at least one modulation parameter based on a function of the previous value and a pseudo-randomly generated number; and
   delivering electrical energy having the pseudo-randomly varied value of the at least one modulation parameter.

3. The method of claim 1, wherein the at least one modulation parameter is pseudo-randomly varied by both increasing and decreasing the value around a mean value of the at least one modulation parameter.

4. The method of claim 1, receiving user-input defining the limited range.

5. The method of claim 1, wherein the modulation parameter comprises at least one of a pulse amplitude, a pulse duration, and a pulse rate.

6. The method of claim 1, wherein the pseudo-random variance of the at least one modulation parameter mimics a physiologically relevant signal.

7. The method of claim 1, wherein the at least one varied modulation parameter is a pulse rate greater than 1500 Hz or a pulse width less than 100 µs.

8. The method of claim 1, wherein the delivered electrical energy is an electrical pulse train.

9. The method of claim 1, further comprising delivering electrical energy in accordance with a plurality of pseudo-randomly varied values of the at least one modulation parameter, such that neural tissue is stimulated without undergoing neurological accommodation that would otherwise occur if the at least one modulation parameter was not pseudo-randomly varied.

10. The method of claim 1, wherein pseudo-randomly varying the value of the at least one modulation parameter includes varying temporal and spatial firing patterns in the tissue of the patient, including varying the pattern around a mean volume of activation (VOA).

11. A neuromodulation system, comprising:
    a plurality of electrical terminals configured for being respectively coupled to a plurality of electrodes;
    modulation output circuitry configured for delivering electrical energy to the electrical terminals in accordance with at least one modulation parameter; and
    control circuitry configured for controlling the modulation output circuitry to provide a sub-threshold therapy to a patient, including delivering the electrical energy at a sub-threshold level such that the delivered electrical energy is not perceived by the patient but is therapeutically effective for the sub-threshold therapy, wherein the control circuitry is configured to pseudo-randomly vary a value of the at least one modulation parameter based on a previous value of the at least one modulation parameter, wherein the at least one modulation parameter is pseudo-randomly varied within a limited range to continually maintain the delivered electrical energy at the sub-threshold level in which the delivered electrical energy is therapeutically effective for the sub-threshold therapy and is not perceived by the patient.

12. The neuromodulation system of claim 11, where in the control circuitry is further configured for calculating the pseudo-randomly varied value of the at least one modulation parameter based on a function of the first value and a pseudo-randomly generated number, and controlling the modulation output circuitry to deliver electrical energy having the pseudo-randomly varied value of the at least one modulation parameter.

13. The neuromodulation system of claim 11, wherein the control circuitry is further configured for pseudo-randomly varying the at least one modulation parameter by both increasing and decreasing the value around a mean value of the at least one modulation parameter.

14. The neuromodulation system of claim 11, wherein the control circuitry is further configured for defining the limited range.

15. The neuromodulation system of claim 11, further comprising a user interface configured for receiving user input defining the limited range.

16. The neuromodulation system of claim 11, wherein the pseudo-random variance of the at least one modulation parameter mimics a physiologically relevant signal.

17. The neuromodulation system of claim 11, wherein the modulation parameter comprises at least one of a pulse amplitude, a pulse duration, and a pulse rate.

18. The neuromodulation system of claim 11, wherein the at least one varied modulation parameter is a pulse rate greater than 1500 Hz or a pulse width less than 100 µs.

19. The neuromodulation system of claim 11, wherein the at least one modulation parameter is pseudo-randomly varied in order to avoid neurological accommodation over time.

20. The neuromodulation system of claim 11, wherein the control circuitry is configured to pseudo-randomly vary the value of the at least one modulation parameter to vary temporal and spatial firing patterns in the tissue of the patient, including varying the pattern around a mean volume of activation (VOA).

* * * * *